(12) United States Patent
Dean et al.

(10) Patent No.: US 6,463,590 B1
(45) Date of Patent: Oct. 15, 2002

(54) APPARATUSES AND RELATED METHODS OF USE OF A UNIVERSAL VISOR COVER

(75) Inventors: Ted M. Dean; William R. Fuller, both of Brenham, TX (US)

(73) Assignee: Tru-Vision Plastics, Brenham, TX (US)

( * ) Notice: Subject to any disclaimer, the term of this patent is extended or adjusted under 35 U.S.C. 154(b) by 0 days.

(21) Appl. No.: 09/950,189

(22) Filed: Sep. 10, 2001

(51) Int. Cl.⁷ .................................................. A61F 9/00
(52) U.S. Cl. ...................................... 2/15; 2/424; 2/434
(58) Field of Search ........................ 2/9, 10, 424, 434, 2/15

(56) References Cited

U.S. PATENT DOCUMENTS

| | | | | |
|---|---|---|---|---|
| 2,511,329 A | * | 6/1950 | Craig | 2/12 |
| 4,076,373 A | * | 2/1978 | Moretti | 2/434 |
| 4,138,746 A | * | 2/1979 | Bergmann | 2/10 |
| 4,563,065 A | * | 1/1986 | Kreissl | 351/47 |
| 4,716,601 A | * | 1/1988 | McNeal | 2/434 |
| 5,592,698 A | * | 1/1997 | Woods | 2/424 |
| 5,673,431 A | * | 10/1997 | Batty | 2/10 |
| 5,970,514 A | * | 10/1999 | Wang-Lee | 2/10 |
| 6,085,358 A | * | 7/2000 | Cogan | 2/424 |

FOREIGN PATENT DOCUMENTS

GB        2349232        * 10/2000

* cited by examiner

Primary Examiner—Rodney M. Lindsey
(74) Attorney, Agent, or Firm—The Matthews Firm

(57) ABSTRACT

An improved apparatus and/or system and method of use is disclosed for a lens for covering at least a portion of a ANSI Z87.1 approved full face shield that fits any mounting that has at least one post and/or bracket.

22 Claims, 2 Drawing Sheets

ND RELATED METHODS
APPARATUSES AND RELATED METHODS OF USE OF A UNIVERSAL VISOR COVER

TECHNICAL FIELD

The present invention relates generally to an improved method and related apparatus for protecting and enhancing the vision of a user through an ANSI Z87.1 approved face shield. Generally, varying embodiments of the present invention utilize one or more stacked layers of a lens that may be selectively removed from a face shield.

BACKGROUND ART

As used herein the term universal mounting means and refers to a lens and/or face shield that fits a variety of mounting bracket, helmet, headgear, and/or the like including, but not limited to mounting brackets made by Fibre-Metal, Jackson, Bullard, MSA, CREWS, TECHNA, OBERON, AMERICAN ALLSAFE, and/or the like. It is common in the art field for a universal mounting to mean and include a face shield attachment or face shield mounting portion that fits more than one style, type, manufacturer, brandname, and/or the like of brackets. A visor that is referred to a universal visor has a plurality of holes and/or throughpassages for attachment to a mounting brackets of a variety of different manufacturers. However, there are a variety of visors that are common in the art that may not have a plurality of holes and/or throughpassages that are commonly made to fit only one specific visor.

A face shield and/or lens having a universal mounting and/or universal attachment portion is well known in the art field and is commonly used because of the wide array of brackets that may be associated with head gear, such as a full face shield and/or a partial face shield manufactured and/or made by any of a plurality of manufacturers as heretofore mentioned, but not necessarily limited to those manufacturers. The use of a universal face shield and/or lens with a universal mounting and/or universal attachment portion allows other manufacturers to manufacture face shields and/or lenses that can fit a plurality of brackets and/or bracket systems. In response, often bracket manufacturers change a bracket arrangement to prevent other manufacturers from constructing devices that fit on the manufacturers brackets. Lens and visor manufacturers compensate for this by adjusting their mode of manufacture to fit the changed design. However, various embodiments of the present invention will fit any mounting bracket and therefore have a universal mounting and/or universal attachment portion.

Transparent or semi-transparent (tinted) face shields for helmets, brackets, and/or the like have become a necessity in many occupations today, from the race car drivers to construction workers. For example, an operator, such as, a motorcycle driver, race car driver, construction worker, fabrication worker, grinder, painter, abrasive blaster, water blaster, and the like all may wear, at one time or another, a face shield. The face shield worn by the operator may become dirty and/or contaminated by oil, grease, sand, dirt, dust, mud, paint, sparks, metal filings, rock, and the like that is constantly flung towards the face and eye region of the operator. Consequently, these shields become dirty very quickly and require downtime, non-working, or non-productive time, to clean, remove, or clear an area of vision for the operator. In response, many prior art devices have evolved as attempted solutions to these problems and/or difficulties.

One such device is found in U.S. Pat. No. 4,138,746 to Bergmann. This patent discloses a motorcycle helmet face shield with a plurality of thin transparent lenses attached to the visor of the helmet. The lenses may be removed by grasping a grasping ear portion along a side of the helmet. The lenses are secured to the motorcycle helmet visor at posts along the sides of the visor. The '746 patent does not disclose a lens that covers all or part of an ANSI Z87.1 full face safety visor having universal mountings that be selectively removed with a tab. Further, this patent only discloses a lens for a motorcycle helmet, or a helmet that encompasses the entire head of a user. Accordingly, the art field is in search of a lens that covers at least a portion of an ANSI Z87.1 full face shield of a visor of a user that utilizes either a standard or a universal bracket mounting system and allows for ease of removal.

Another prior art patent is U.S. Pat. No. 5,592,698 to Woods. This patent discloses another lens system for a motorcycle helmet. The lens fits across the face shield of a motorcycle helmet and has tabs. The tabs have a surface interruption means comprising a plurality of spaced apart projections disposed on said tab. Accordingly, the art field is in search of a lens that covers at least a portion of an ANSI Z87.1 full face shield of a visor of a user that utilizes either a standard or a universal bracket mounting system and allows for ease of removal.

Another prior art patent is U.S. Pat. No. 4,455,689 to Boyer. This patent discloses goggles with a tear off transparencies. The patent requires a goggle with a special bracket that is inserted through the strap slot at one side of a goggle frame for securing the tear off transparencies. The transparencies are configured with an arm portion that is exposed as the transparency becomes the outermost transparency. This patent does not disclose a lens that has a universal mounting or a system for mounting that would fit on a universal bracket that may be easily removed. Accordingly, the art field is in search of a lens that covers at least a portion of an ANSI Z87.1 full face shield of a visor of a user that utilizes either a standard or a universal bracket mounting system and allows for ease of removal.

Another prior art patent is U.S. Pat. No. 6.085,358 to Cogan. This patent discloses a vision enhancing tear off shield guard system for use with the visor of a racing helmet. This patent does not disclose a lens that has a universal mounting or a system for mounting that would fit on a universal bracket while allowing for ease of removal. Accordingly, the art field is in search of a lens that covers at least a portion of an ANSI Z87.1 full face shield of a visor of a user that utilizes either a standard or a universal bracket mounting system and allows for ease of removal.

U.S. Pat. No. 4,716,601 to McNeal discloses a tear off lens system for goggles. This patent does not disclose a lens that has a universal mounting or a system for mounting that would fit on a universal bracket while allowing for ease of removal. Accordingly, the art field is in search of a lens that covers at least a portion of an ANSI Z87.1 full face shield of a visor of a user that utilizes either a standard or a universal bracket mounting system and allows for ease of removal.

Another prior art patent is U.S. Pat. No. 4,076,373. This patent discloses a method and means for shielding the lens of a face mask. The patent provides a lens that covers an enlarged aperture in a helmet. The helmet covers the entire head of the user and the aperture is provided opposite the eyes. The lens are arranged in a position over the aperture of the helmet. This patent does not disclose a lens that has a universal mounting or a system for mounting that would fit on a universal bracket while allowing for ease of removal.

Accordingly, the art field is in search of a lens that covers at least a portion of an ANSI Z87.1 full face shield of a visor of a user that utilizes either a standard or a universal bracket mounting system and allows for ease of removal.

SUMMARY OF THE INVENTION

The present invention generally relates to apparatuses and/or systems comprising a lens that covers at least a portion of any ANSI Z87.1 approved face shield. related devices, and methods of use. Various embodiments of the present invention are configured to fit both lenses with a standard or a universal mounting configuration of various manufacturers.

This summary is not intended to be a limitation with respect to the features of the invention as claimed, and this and other objects can be more readily observed and understood in the detailed description of the preferred embodiment and the claims.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

GENERAL DESCRIPTION AND PREFERRED MODE FOR CARRYING OUT THE INVENTION

Figure 1:
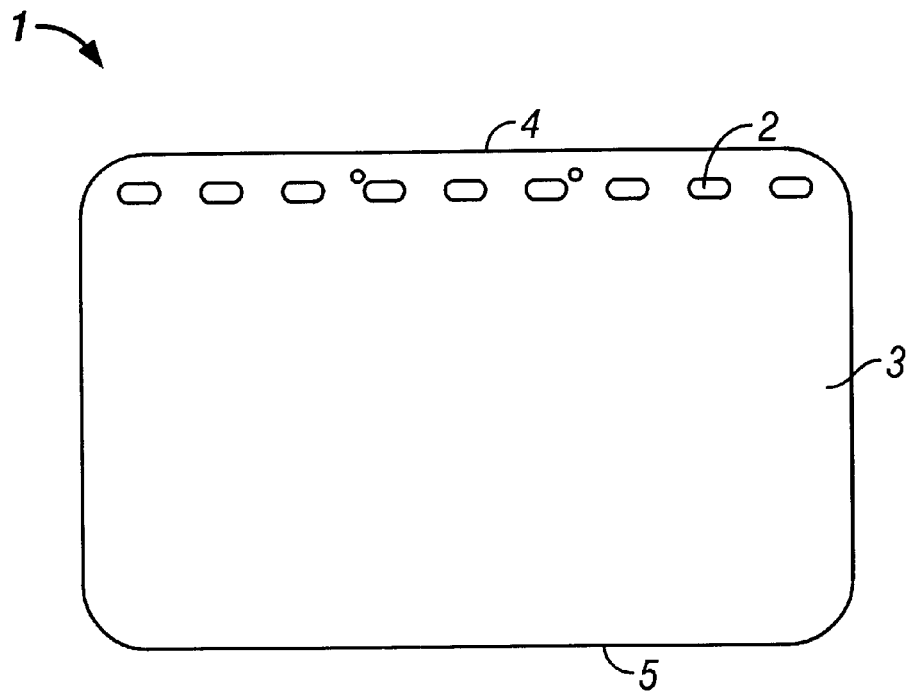
FIG. 1 is an illustration of an embodiment of a universal face shield.

Now referring to FIG. 1, an illustration of an embodiment of a universal face shield, is a common form of a face shield is illustrated. Face shield 1 has apertures 2 located about a first edge 4. The shape of face shield 1 is generally defined by a second edge 5. In an embodiment, face shield 1 is quadrangular in shape. In an alternate embodiment, face shield 1 is elliptical in shape. However, face shield 1 may be of any shape common in the art and various other shapes will be readily apparent to those of ordinary skill.

Face shield 1 is generally at least partially a sheet 3. Sheet 3 is generally composed of a plastic pliable material. In an embodiment, sheet 3 is between about 5 to about 25 thousandths of an inch thick. In another embodiment, sheet 3 is between about 3 and about 50 thousandths of an inch thick. However, various other ranges of thickness may be used. For example. in an alternate embodiment, sheet 3 is of a sufficient thickness that sheet 3 is capable of withstanding mild impactive forces. Impactive forces being those forces caused by impacts, whether from sand, gravel, dirt, mud, tools, poles, paint, cords, chemicals, and the like. In another embodiment, sheet is of a sufficient thickness to withstand medium to strong impactive forces. It is contemplated that as the risk of increasing impactive forces increases from mild to medium to strong, the thickness of the lens should be increased. Accordingly, various embodiments of the present invention may use face shields of any thickness.

Various components may be used to construct a face shield. In an embodiment, sheet 3 may be composed of a Glycol Modified Polyethylene Terephthalate (PETG). PETG is a highly durable material that withstands shocks. As well, PETG reacts well with heat and may be formed into any desired shape. In an embodiment, the PETG selected is clear. In an alternate embodiment, the PETG selected is tinted, i.e. translucent, but not completely clear. In an embodiment, sheet 3 is composed of PETE, or a low grade version of PETG. The PETE used should be at least partially translucent. In another embodiment, sheet 3 is composed of a PVC. The PVC should be at least partially translucent. In an alternate embodiment, sheet 3 is composed of a RPET, a recycled polyethylene terephthalate. The RPET should be at least partially translucent. As well, the present invention contemplates various other components and mixtures of components from which to form a face shield.

About the first edge 4 of face shield 1, a plurality of apertures 2 allow for face shield 1 to be connected to any bracket mounting on a helmet and/or a headgear. Such plurality of apertures is commonly referred to as a universal mounting and/or universal mounting attachment portion.

Figure 4:
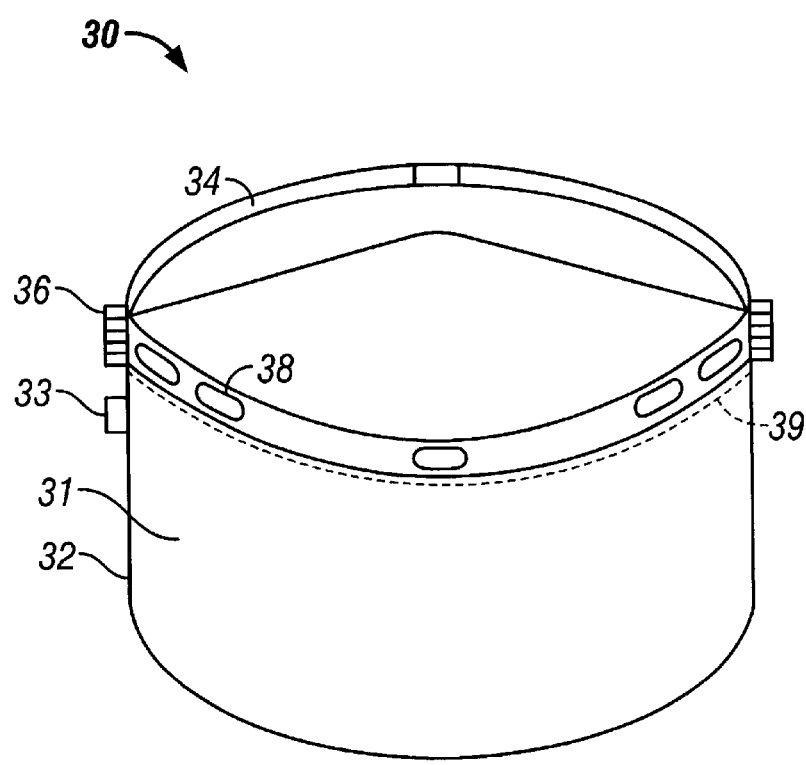
FIG. 4 is an illustration of an embodiment of the present invention laid over a face shield and connected to head-gear.

Generally, the face shield is provided with a plurality of apertures 2 in differing arrangements such that the face shield may be connected on a varying arrangements of posts on a head gear (not shown) as will be more fully discussed in reference to FIG. 4. Apertures 2 may be in any arrangement and of varying number and still be a universal arrangement.

Figure 2:
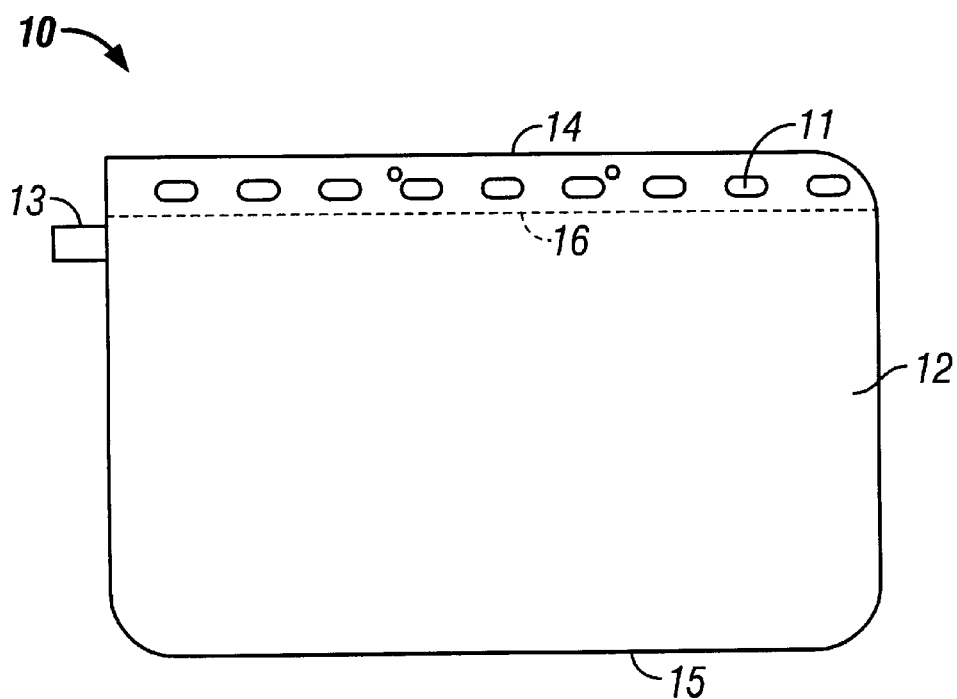
FIG. 2 is an illustration of an embodiment of a lens of the present invention.

Now referring to FIG. 2, an illustration of an embodiment of a lens of the present invention, the general conforming shape of the lens 10 to the face shield 1 may be observed. Lens 10 is generally defined by a lens sheet 12 having a first conforming edge 14 and a second conforming edge 15. In an embodiment of the present invention, sheet 12 completely covers the face shield 1. In another embodiment of the present invention, sheet 12 covers at least a portion of face shield 1. Various embodiments of the type that cover at least a portion of face shield 1 cover only a portion of face shield 1 about a line of sight of an operator. Various lines of sight may be protected. In an embodiment, the line of sight is directly in front of the operator. In another embodiment, the line of sight is downward.

Lens 10 may be applied singularly to a face shield or may be applied in a plurality of lenses 10. An embodiment of the present invention utilizes a single lens 10 connected to a face shield. Another embodiment uses a plurality of lenses 10 connected to a face shield. A plurality of lenses 10 ranges from 2 to an infinite number. However, the type of material used to construct lens 10 and the number of lenses 10 connected to a face shield may vary and is limited by visibility through lens 10. In that regard, the number of lenses 10 connected to the face shield should not be such that vision of a user or wearer is adversely affected. Adversely affected is defined to mean when the vision of the worker through lenses 10 is reduced and/or altered such that the worker is no longer able to work safely in the task assigned.

Located about first conforming edge 14 is a plurality of apertures. The plurality of apertures 11 are arranged in a fashion to fit any universal face shield, as will be more fully described in reference to FIG. 4. An embodiment of the present invention utilizes lens 10 apertures 11 that generally conform to apertures of a face shield. However, other embodiments of the present invention have lens 10 apertures 11 that do not generally conform to apertures of a face shield.

Various embodiments of the present invention have a tab 3 to assist in removal of sheet 12. A user or wearer may grasp sheet tab 13 and remove sheet 12 by a ripping or tearing of perforation 16. In this manner, sheet 12 may be removed from a face shield (not shown) while leaving other lenses 10 connected to the face shield 1. Perforation 16 allows for ease of removal without the necessity of disconnecting lens 10 from the head gear to which it mounted to discard it as it becomes dirty.

In another embodiment, tab 13 is only exposed on the outermost lens 10 of a plurality of lenses 10 connected to a head gear. In this manner, a user or wearer may grasp tab 13 and remove lens sheet 12 along perforation 16 without any risk of removing more than one of lens sheet 12. Tab 13 is folded under an adjacent lens sheet 12 and revealed when the adjacent lens sheet 12 is removed. Tab 13 of outermost lens sheet 12 is revealed after installation.

Lens 10 may be constructed of any material common in the art. In various embodiments, lens 10 fits any and/or most ANSI Z87.1 approved face shield. In other embodiments, lens 10 fits any and/or most ANSI Z87.1 approved face shield with a universal mounting configuration. In other embodiments, lens 10 fits any and/or most ANSI Z87.1 approved face shield with a standard mounting configuration. In another embodiment, lens 10 fits any mounting face shield. In an embodiment, lens 10 may be composed of a Glycol Modified Polyethylene Terephthalate (PETG). PETG is a highly durable material that withstands shocks. As well, PETG reacts well with heat and may be formed into any desired shape. In an embodiment, the PETG selected is clear. In an alternate embodiment, the PETG selected is tinted, i.e. translucent, but not completely clear. In an embodiment, lens 10 is composed of PETE, or a low grade version of PETG. The PETE used should be at least partially translucent. In another embodiment, lens 10 is composed of a PVC. The PVC should be at least partially translucent. In an alternate embodiment, lens 10 is composed of a RPET, a recycled polyethylene terephthalate. The RPET should be at least partially translucent. As well, the present invention contemplates various other components and mixtures of components from which to form a lens. Other embodiments of the present invention incorporate a tint to lens 10. Other embodiments include a tint to all of a plurality of lenses 10. Further, still other embodiments incorporate a tint to less than the plurality of lenses, such that not every lens is tinted.

Embodiments of the present invention have a lens sheet at a thickness in the range of 0.25 thousandths of an inch to five (5) thousandths of an inch. However, other embodiments have a thickness ranging from 0.05 thousandths of an inch to ten (10) thousandths of an inch. The thickness chosen by a user or wearer will depend on a variety of factors that are readily known and apparent to those of skill in the art, such as the operational application. A greater thickness may be desired in extreme conditions and a thinner application for less extreme conditions.

Figure 3:
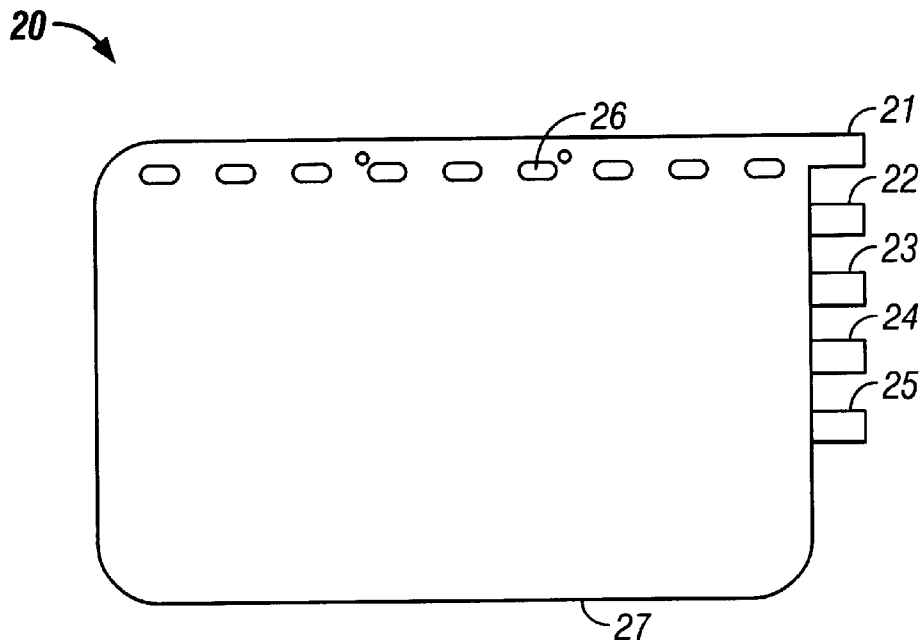
FIG. 3 is an illustration of an alternate embodiment of a lens of the present invention.

Now referring to FIG. 3, an illustration of an alternate embodiment of a lens of the present invention, an arrangement of cascading tabs (21–25) is illustrated on a lens 20. As well, the embodiment illustrated does not include a perforation, however, other embodiments of the cascading tabs (21–25) may have a perforation located across lens sheet 27 such that a user or wearer may grasp a tab (21–25) and remove lens sheet 27 as herein described. In an embodiment with a cascading tabs (21–25), a user or operator may remove a desired number of lens sheets 27 from a face shield while leaving other lens sheets connected to the face shield.

Now referring to FIG. 4, an illustration of an embodiment of the present invention connected to head-gear, a head gear and face shield is illustrated with lens sheet(s) 31 connected. Head Gear 35 is a common prior art head gear. Many modifications in arrangements of the head gear will become readily apparent to those of ordinary skill in the art and are still contemplated within embodiments of the present invention. Generally, the head gear 35 used with embodiments of the present invention have a post(s) 37 in an arrangement conforming to a face shield 32 mounting system.

A face shield 32 is connected to head gear 35 by post(s) 37. Post(s) 37 may be post with end caps, posts with a deformable member, screw type posts or any other post that is well known in the art field. In an embodiment, face shield 32 is releasably connected to head gear 35 and a lens 31 is applied so as to at least partially cover face shield 32 and connected with post(s) 37 through aperture(s) 38. The materials for construction disclosed herein have an affinity for releasably engaging face shield 32 to provide a secure fit between face shield 32 and lens 31. Various embodiments use a lens 31 of varying shape that may extend over a portion of either the first or the second conforming edge. Other embodiments use a lens 31 that does not generally conform to a first or second edge and may be any shape.

As a wearer or user is wearing head gear 35, lens sheet 31 may be removed as it becomes dirty or the vision of the user or wearer becomes occluded by grasping tab 33 and removing lens sheet 31 by tearing along perforation 39. In this manner, the wearer or user may maintain good vision through a lens that may be clean without the necessary stoppage of work required to change face shield 32.

While only a few embodiments have been illustrated, other modifications and embodiments will be readily apparent to those of ordinary skill in the art. Such modifications are fully intended to be covered by this disclosure.

What is claimed is:

1. A tear-away lens system comprising:
   a face shield having a first edge and a second edge, a plurality of apertures about the first edge; and,
   a lens generally conforming to at least a portion of a shape of the face shield having generally a first conforming edge and a second conforming edge, the lens having a tab; and, a plurality of generally conforming apertures about the first conforming edge, wherein the apertures allow the face shield and the lens to be connected to a head gear and/or a helmet mounting bracket.

2. The system of claim 1 further comprising a perforation line.

3. The system of claim 2 wherein the perforation line is along a portion of the lens.

4. The system of claim 1 wherein the lens is transparent.

5. The system of claim 1 wherein the tab is connected about the second conforming edge.

6. The system of claim 1 further comprising a visor head gear.

7. The system of claim 6 further comprising a locking means connected about the visor head gear for releasably attaching the face shield and the lens.

8. The system of claim 1 wherein the lens further comprises a plurality of lenses.

9. The system of claim 1 wherein the lens is flexible.

10. The system of claim 1 wherein the lens is tinted.

11. The system of claim 1 wherein the lens is constructed of a material selected from the group consisting of PET, PETG, PETE, RPET, HIPS, polyester and PVC or combinations thereof.

12. A new and improved removable lens comprising:
    a lens having an upper end and a lower end for at least partially covering a face shield, the upper end adapted for connection to a mounting selected from the group consisting of a standard mounting and a universal mounting, on a full face shield;

a perforation line along a portion of the lens; and, a tab connected to the lens.

13. The system of claim 12 further comprising a head gear.

14. The system of claim 13 further comprising a plurality of lenses.

15. The system of claim 13 wherein the tab is connected below the perforation.

16. The system of claim 13 wherein the portion covered by the lens is a line of sight of an operator.

17. The system of claim 14 wherein at least one lens is tinted.

18. The system of claim 14 wherein each of the plurality of lenses has a tab.

19. The system of claim 18 wherein the tabs are cascading.

20. The system of claim 16 wherein the line of sight is in front of the operator.

21. The system of claim 13 wherein the tab further comprises surface interruptions.

22. The system of claim 12 further comprising a visor.

* * * * *